United States Patent
Chahine et al.

(10) Patent No.: US 12,383,182 B2
(45) Date of Patent: Aug. 12, 2025

(54) MULTI-SENSOR RESISTIVE TEXTILE ECG SYSTEM

(71) Applicant: MYANT INC., Toronto (CA)

(72) Inventors: Tony Chahine, Toronto (CA); Milad Alizadeh-Meghrazi, Toronto (CA)

(73) Assignee: Myant Inc., Toronto (CA)

(*) Notice: Subject to any disclaimer, the term of this patent is extended or adjusted under 35 U.S.C. 154(b) by 471 days.

(21) Appl. No.: 17/292,666

(22) PCT Filed: Nov. 12, 2018

(86) PCT No.: PCT/IB2018/058877
§ 371 (c)(1),
(2) Date: May 10, 2021

(87) PCT Pub. No.: WO2020/099906
PCT Pub. Date: May 22, 2020

(65) Prior Publication Data
US 2022/0007986 A1    Jan. 13, 2022

(51) Int. Cl.
*A61B 5/304*    (2021.01)
*A61B 5/00*    (2006.01)
(Continued)

(52) U.S. Cl.
CPC .............. *A61B 5/304* (2021.01); *A61B 5/27* (2021.01); *A61B 5/282* (2021.01); *A61B 5/6804* (2013.01);
(Continued)

(58) Field of Classification Search
None
See application file for complete search history.

(56) References Cited

U.S. PATENT DOCUMENTS

2010/0041975 A1    2/2010    Chen et al.
2011/0288605 A1    11/2011    Kaib et al.
(Continued)

FOREIGN PATENT DOCUMENTS

CN    107205678 A    9/2017
EP    3634215 A1    4/2020
(Continued)

OTHER PUBLICATIONS

European Patent Office, Extended European Search Report for European Patent Application No. 18940268.8, dated Jun. 15, 2022.
(Continued)

*Primary Examiner* — Ankit D Tejani
(74) *Attorney, Agent, or Firm* — Norton Rose Fulbright Canada LLP

(57) ABSTRACT

An ECG sensor system comprising: a substrate having a first side and a second side, the substrate of a non-conducting material; a plurality of textile-based sensors positioned on the first side, each of the plurality of textile-based sensors spaced apart from one another on the first side, the second side covering one side of the each of the plurality of textile-based sensors as an insulating covering, the each of the plurality of textile-based sensors including conductive fibres interlaced with one another; and a conductive trace connected to the each of the plurality of textile-based sensors, each of the conductive traces for connecting the plurality of textile-based sensors to an electronic controller for sending and receiving electronic signals from a selected pair of the plurality of textile-based sensors.

11 Claims, 9 Drawing Sheets

(51) Int. Cl.
  A61B 5/27     (2021.01)
  A61B 5/282    (2021.01)
  D03D 1/00     (2006.01)
  D03D 15/00    (2021.01)
  D03D 15/283   (2021.01)
  D03D 15/533   (2021.01)
  D04B 1/14     (2006.01)
  D04B 1/22     (2006.01)

(52) U.S. Cl.
  CPC ........... *D03D 1/0088* (2013.01); *D03D 15/00* (2013.01); *D03D 15/283* (2021.01); *D03D 15/533* (2021.01); *D04B 1/14* (2013.01); *D04B 1/22* (2013.01); *A61B 2562/164* (2013.01)

(56)       References Cited

U.S. PATENT DOCUMENTS

| | | | |
|---|---|---|---|
| 2013/0131460 A1 | 5/2013 | Yuen | |
| 2016/0287128 A1* | 10/2016 | Jain | A61B 5/282 |
| 2017/0056644 A1 | 3/2017 | Chahine et al. | |
| 2017/0079348 A1 | 3/2017 | Chahine et al. | |
| 2017/0265763 A1 | 9/2017 | Gazzoni et al. | |
| 2018/0168508 A1 | 6/2018 | Biel et al. | |
| 2018/0344171 A1 | 12/2018 | Straka et al. | |
| 2019/0223739 A1 | 7/2019 | Rapin et al. | |

FOREIGN PATENT DOCUMENTS

| | | |
|---|---|---|
| JP | 2013528070 A | 7/2013 |
| WO | 2016044933 A1 | 3/2016 |
| WO | 2017045062 A1 | 3/2017 |
| WO | 2018161152 A1 | 9/2018 |

OTHER PUBLICATIONS

PCT, Written Opinion and International Search Report of International Application No. PCT/IB2018/058877, mailing date Jul. 26, 2019.
Japanese Patent Office, Office Action dated Sep. 27, 2022 for Japanese Patent Application No. 2021-525249.
Japanese Patent Office, Notice of Allowance dated Mar. 28, 2023 for Japanese Patent Application No. 2021-525249.
Chinese Patent Office, Office Action dated Nov. 20, 2023 for Chinese Patent Application No. 201880099803.3.
Stahl, Ted, "What Embroiderers Should Know About Thermo-FLOCK", URL: https://www.tedstahl.com/what-embroiderers-should-know-about-thermo-flock/, Apr. 18, 2018.
Communication pursuant to Article 94(3) EPC issued in connection with European Patent Application No. 18 940 268.8 on Nov. 14, 2023.

* cited by examiner

MULTI-SENSOR RESISTIVE TEXTILE ECG SYSTEM

FIELD

The present disclosure relates to ECG sensors for smart textiles.

BACKGROUND

The existing wearables in the market for measuring ECG signals (specifically for health applications) are limited to record from fixed locations. Any noise (or artifact) can attenuate the recorded signal. As well, these wearables cannot be used for research purposes as they are limited to specific locations on the body. Further, the existing ECG data acquisition tools (non-wearables) which have been widely used for medical applications can record high quality ECG signals from different locations on the body. These data acquisition tools use gel-electrodes to record ECG signals. Thus, they suffer from (a) need for clinician to supervise the recording from patients, (b) need for skin preparation and (c) need for stable position to connect electrode wires to the patients (they cannot be used for continuous recording of ECG signals on the daily basis).

While current non-fibre gel electrodes are useful in collecting ECG signals, woven or knit ECG sensors suffer from the disadvantage of intermittent or sub optimal contact with the wear's skin. Thus, a textile-based sensor cannot measure ECG signals with a desired resolution as they are limited to a particular location of the body, such that appropriate measurement resolution is hampered by inherent lack of firm skin contact during measurement. Thus, collection of necessary ECG features for heart-related diagnosis may not achievable by a woven, knit, electrode.

Therefore, as observed, current gel electrodes can be used to provide better signal quality with lower impedance as compared to textile-based electrodes. However gel electrodes also suffer from potential skin allergy (if uses for a long time), must firmly and at all times attach to the body (e.g. using adhesives), requires complex wiring, and requires skin preparation by clinical professionals in advance (as well as during) of signal collection.

SUMMARY

It is an object of the present invention to provide system of textile-based electrodes and sensors applicable to ECG measurement to obviate or mitigate at least one of the above presented disadvantages.

Multi sensor textile-based ECG platform (e.g. band) measures ECG signals with desired resolution from different locations of the patient's body to facilitate appropriate measurement when firm skin contact is not possible for all the electrodes simultaneously. Furthermore, this platform provides additional chances to collect necessary ECG features for heart-related diagnosis which are not achievable by a single electrode.

Advantages of using multiple textile electrodes for ECG measurement can include: provides reasonably good signal quality; biocompatible (no skin allergy); higher impedance than traditional gel electrodes; touches body; little skin preparation; can work wirelessly; can be incorporated into textiles, making the possibility of being used as a wearable and therefore reusable.

A first aspect provided is an ECG sensor system comprising: a substrate having a first side and a second side, the substrate of a non-conducting material; a plurality of textile-based sensors positioned on the first side, each of the plurality of textile-based sensors spaced apart from one another on the first side, the second side covering one side of the each of the plurality of textile-based sensors as an insulating covering, the each of the plurality of textile-based sensors including conductive fibres interlaced with one another; and a conductive trace connected to the each of the plurality of textile-based sensors, each of the conductive traces for connecting the plurality of textile-based sensors to an electronic controller for sending and receiving electronic signals from a selected pair of the plurality of textile-based sensors.

BRIEF DESCRIPTION OF THE DRAWINGS

The foregoing and other aspects will now be described by way of example only with reference to the attached drawings, in which.

DETAILED DESCRIPTION

Figure 1:
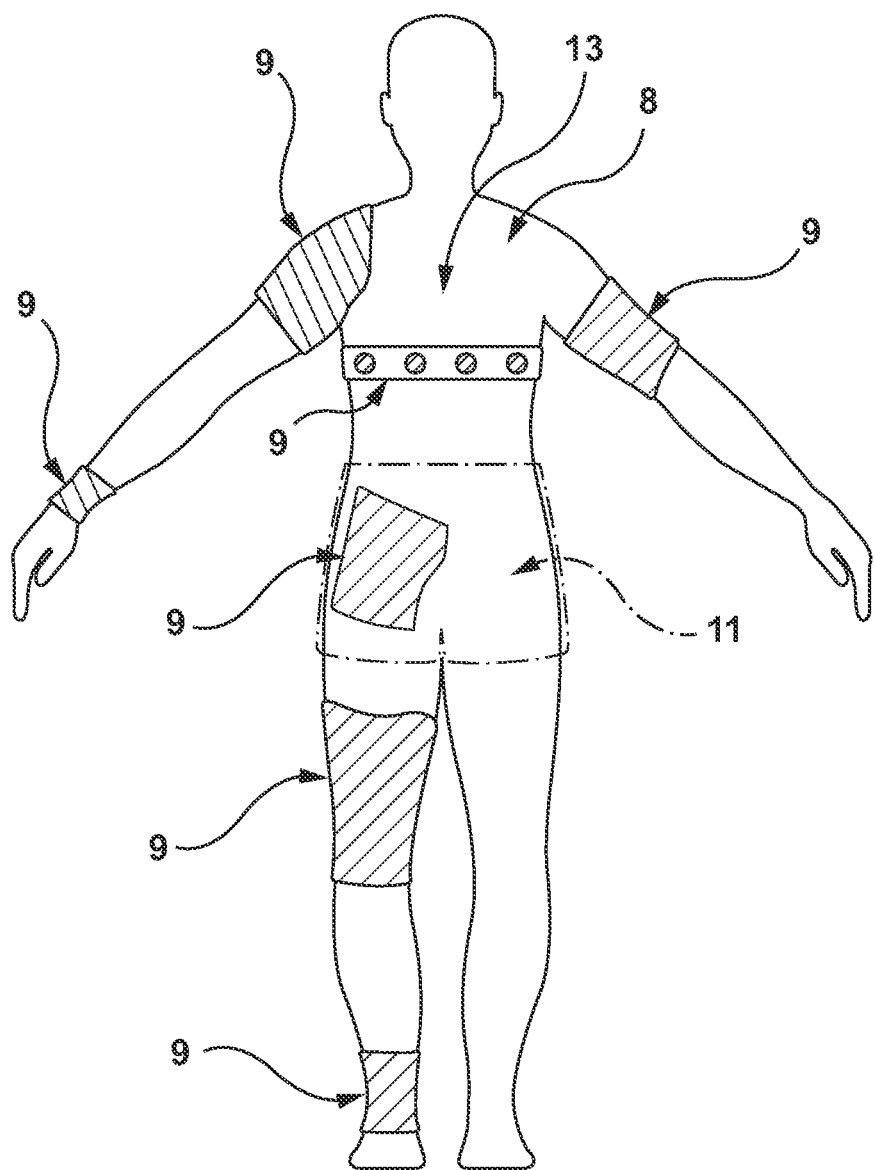
FIG. 1 is system view of textile examples for wearing or otherwise positioning adjacent to a body of a wearer.

Referring to FIG. 1, shown is a body 8 of a wearer for wearing one or more textile based computing platforms 9 positioned about one or more regions (e.g. knee, ankle, elbow, wrist, hip, shoulder, neck, etc.) of the body 8. For sake of simplicity, textile based computing platforms 9 can also be referred to as textile computing platforms 9. For example, the textile computing platforms 9 can also be referred to as a wrist sleeve 9, a knee sleeve 9, a shoulder sleeve 9, an ankle sleeve 9, a hip sleeve 9, a neck sleeve 9, a chest sleeve, etc. It is also recognised that the sleeve can be referred to as a band. It is also recognized that the textile computing platform 9 can be incorporated as part of a larger garment 11 (e.g. a pair of briefs 11 as shown in ghosted view for demonstration purposes only). It is recognized that the garment 11 could also be a shirt, pants, body suit, as desired. As such, a fabric/textile body 13 of the garment 11 can be used to position the textile computing platform 9 for selected areas of the body 8. In other words, the textile computing platform 9 contains a number of textile computing components, e.g. sensors/actuators 18, electronic circuits 17, controller 14—see FIG. 2, which are all incorporated into or otherwise mounted on a fabric/textile body 13 of the garment 11. It is also recognised that the textile computing platform 9 can be incorporated into a textile 11 (e.g. a fabric sheet, a covering, or other fabric structure) that is not worn by the body 8, rather is positioned adjacent to the body 8. Examples of the textile 1 can include bedsheets, seat coverings (e.g. car seat), etc. In terms of uses for the textile computing platform 9, it is envisioned that one or more textile computing platforms 9 can be distributed (e.g. worn) about the body 8 of the user. Whether embodied as a single or multiple textile computing platforms 9, it is envisioned that the textile computing platform(s) 9 provide for multiple sensors/electrodes 18 for positioning about the body strategically in order to measure ECG signals, for example, which need appropriate contact with the skin of the body 8. As further described below, a multi-sensor 18 system 19 is provided such that a controller 14 can determine which of the sensors/electrodes 18a,b,c,d of the multi-sensor system 19 are out of contact with the skin and thus are discarded as signal generators 6a/receivers 6b for the generation/collection of ECG signals 6a,6b of desired resolution while utilizing the collection (e.g. system 19) the textile-based sensors/electrodes 18a,b,c,d—see FIG. 2.

Referring again to FIGS. 1 and 2, the textile computing platform 9 can be integrated with the textile/fabric body 13 (e.g. a plurality of fibres/threads/yarn interlaced as woven and/or knitted, as desired). The textile computing platform 9 has the controller 14 for sending/receiving signals to one or more sensors/actuators 18 distributed about the body 13. The shape of the sensors/actuators 18 can be elongate (e.g. as a strip extending in a preferred direction) or can extend as a patch in a plurality of directions (e.g. extend side to side and end to end). The signals are transmitted between the sensors/actuators 18 and the controller 14 via one or more electronic circuits 17 connecting the controller 14 to each of the sensors/actuators 18. It is also recognized that the electronic circuits 17 can also be between individual pairs of the sensors/actuators 18, as desired. As further described below, the sensors/actuators 18 can be textile based, i.e. incorporated via interlaced (e.g. knitting, weaving) as integral to the material structural integrity of the fabric layer of the body 13 (formed as a plurality of interlaced threads of electrically conductive and optionally non-conductive properties). Further, the electronic circuits 17 (e.g. electrically conductive threads) can also be incorporated/interlaced (e.g. knitting, weaving, etc.) into/with the adjacent fabric layer of the body 13 (also comprising a plurality of interlaced threads/fibres). The controller 14, further described below, can include a network interface (e.g. wireless or wired) for communicating with a computing device 23 (e.g. smart phone, tablet, laptop, desktop, etc.) via a network 25.

Figure 2A:
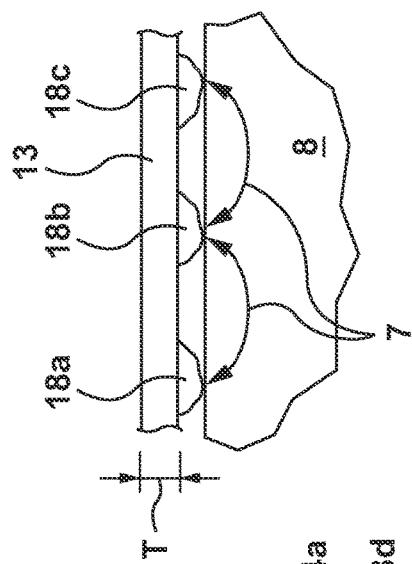
FIGS. 2, 2a are an exemplary view of a textile computing platform of the garment of FIG. 1 incorporated into an article of clothing including a variety of sensors/actuators and conductive pathways.

It is recognised that the conductive fibres 24a of the textile-based sensors 18 can be interlaced with the non-conductive fibres 24b in the body of the base fabric layer 13 (recogniszing that the non-conductive fibres 24b insulate electrically the individual sensors 18 (e.g. sensors 18a,b,c,d of the system 19) from undesirably communicating with one another via the body of the base fabric layer 13. It is desired that the individual sensors 18 communicate 7 with one another via the body 8 of the wearer, as further described below. Referring to FIG. 2a, shown is the electrical signal communication 7 between various sensors 18a,b,c via an electrically conductive pathway of the body 8 of the wearer.

Figure 3A:
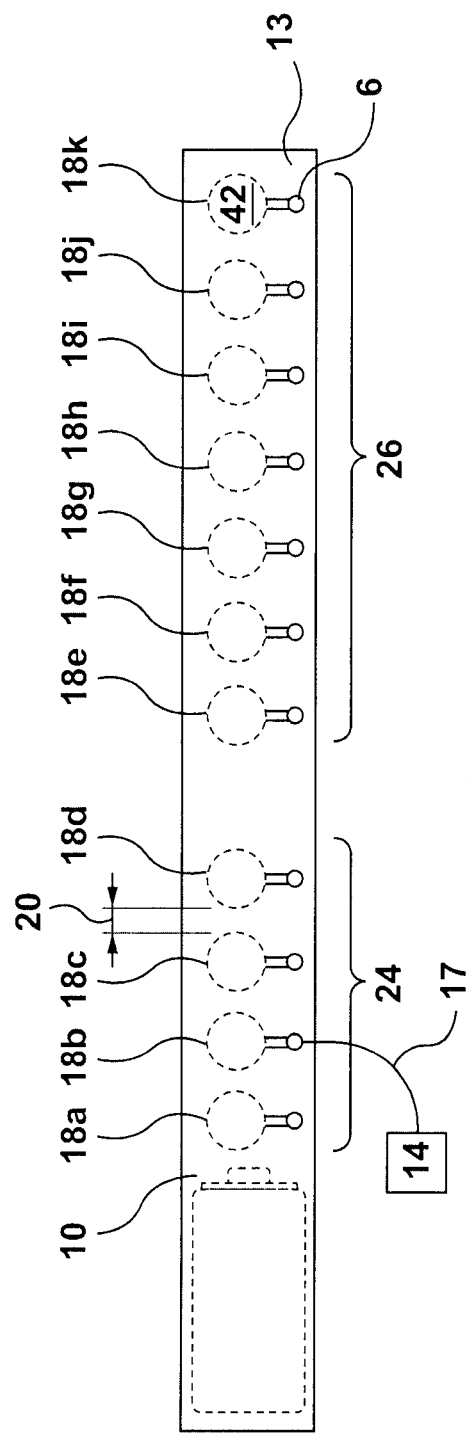
FIG. 3a shows a side view of an embodiment of an ECG sensor system of the textile computing platform shown in FIG. 2.
Figure 3B:
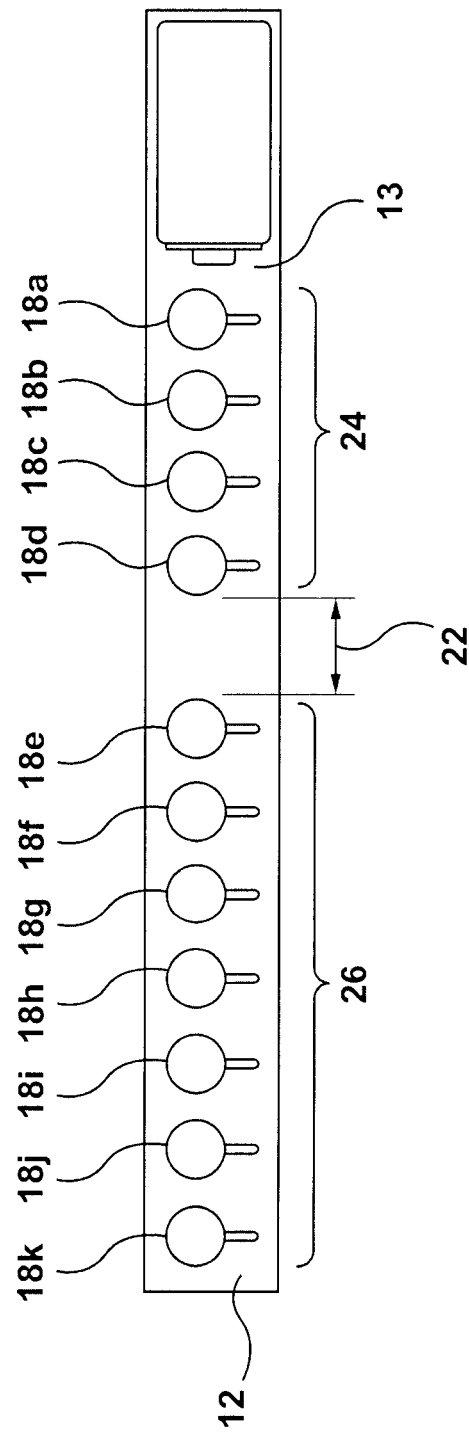
FIG. 3b shows a different side view of the ECG sensor system of the textile computing platform shown in FIG. 2.
Figure 4B:
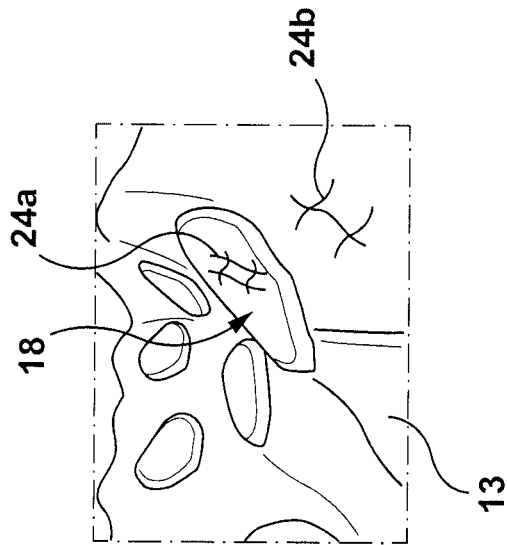
FIG. 4b shows an alternative embodiment of the sensor of FIG. 3b.
Figure 4A:
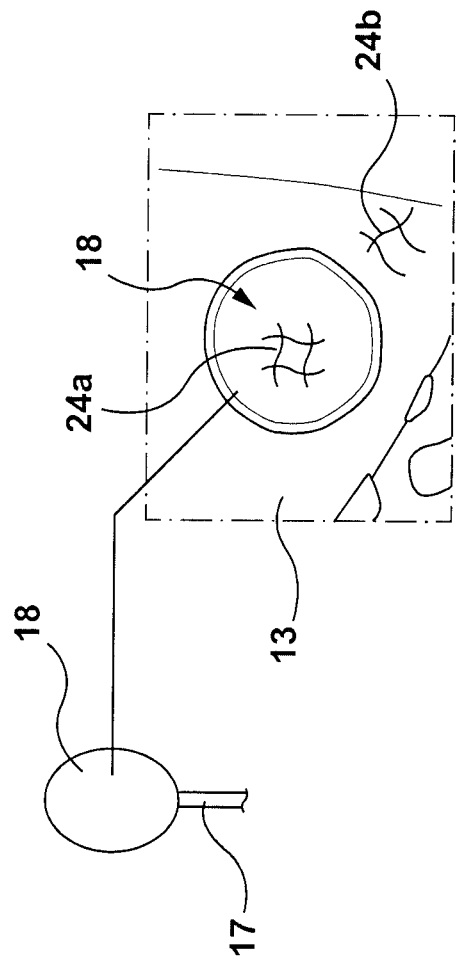
FIG. 4a shows a top view of a sensor of the system of FIG. 3b.

As shown in FIGS. 3a,b, the fabric layer of the body 13 has a first side 10 and a second side 12, such that the sides 10, 12 are opposed to one another (e.g. front and back) with respect to the body 8 of the wearer. For example, the base fabric layer 13 of the "front" or top side 10 has base fibres 24b protecting the sensors/actuators 18 from undesirable contact (e.g. moisture/grounding/etc.) with the environment external to the wearer. In terms of the back side 12, the sensors/electrodes 18 are exposed from the base fabric layer 13 (acting as a substrate—see FIG. 4) so as to provide for direct contact with the skin of the wearer, while at the same time the base fabric layer 13 insulates the sensors/electrodes from one another via intra spacing 20 between the sensors 18 within a group while also having a inter spacing 22 between respective groups. For example, referring to FIGS. 3a,b, generator group 24 contains a set of actuator sensors 18a,b,c,d and receiver group 26 contains a set of receiver sensors 18e,f,g,h,i,j,k. It is recognised that the intra spacing 20 between sensors 18 within a group can be less than the inter spacing 22 between groups (or sets 24,26) of the sensors 18. It is recognised that the intra spacing 20 between sensors 18 within a group can be greater than the inter spacing 22 between groups (or sets 24,26) of the sensors 18. It is recognised that the intra spacing 20 between sensors 18 within a group can be equal to the inter spacing 22 between groups (or sets 24,26) of the sensors 18. In any event, the groups/sets 24,26 of sensors 18 can used to designate function of the sensors 18, for example as discussed having an actuator group 24 and a receiver group 26. It is recognised that the actuator group 24 can have more individual sensors 18 that contained within the receiver group 26. It is recognised that the actuator group 24 can less individual sensors 18 that contained within the receiver group 26. It is recognised that the actuator group 24 can an equal number of individual sensors 18 as contained within the receiver group 26.

In view of the above, as further described below, the controller 14 can utilize one of the sensors 18 from the actuator group 24 and one or more from the receiver group 26 from which to generate the signal 6a and thus collect the signal 6b via the conductive body pathway 7. The collected signal(s) 6b can be examined for appropriate signal quality by the controller 14, recognizing that signals of deemed undesirable quality (e.g. signal amplitude below a set amplitude minimum, signal detail such as below a set number of desired signal characteristics/features present such as peaks, intervals and other ECG indicators—see FIG. 8) would be discarded by the controller 14 and alternative sensors 18 would be selected to use in generating and collecting the signals 6a,b. For example, referring to FIGS. 3a,b the controller 14 can select and generate a signal 6a from sensor 18a (from the actuator group 24) and then collect and receive the signal(s) 6b from one or more of the sensors 18e,f,g,h,i,j,k from the collector group 26. Upon examination of the collected signal(s) 6b, the controller would analyze the signal(s) 6b to determine if they are of acceptable signal quality. If so then the controller 14 could continue to use actuator sensor 18a to generate the signal 6a and the receiver sensor(s) 18e,f,g,h,i,j,k to collect the signal(s) 6b. On the other hand, if none of the collected signal(s) 6b was/were deemed of unacceptable quality, then the controller could decide to select another generator sensor (e.g. sensor 18b) to use as the signal 6a generator. In this manner, the controller 14 can utilize the system of multi-sensors 19 in order to choose pairings of the sensors 18, e.g. an actuator sensor 18a with a receiver sensor 18f, that result in an acceptable collected signal 6b of deemed ECG quality. It is recognised that as discussed above, any of the sensors 18 of the system 19 can change their degree of direct contact with the skin of the wearer during the measurement of the signals 6a,b, for example due to movement of the wearer.

This real time change potential in direct contact between any of the sensors 18 of the system 19 and the skin requires the controller 14 to analyze the collected signals 6b over time and thus decide if a change in sensors 18 being used in the sensor pairing for ECG signal 6a,b collection is needed, in view of determined signal quality. As such, it is recognised that over time, a deemed acceptable sensor 18 pairing (e.g. a selected actuator sensor 18 of the generation group 24 with a selected receiver sensor 18 of the receiver group 26) can be dynamically changed during the ongoing signal generation and collection. It is assumed that deemed signal(s) 6b of poor or unacceptable quality can be due to direct skin contact of any sensor 18 being below a set contact standard or contact limit/threshold. For example, the set contact standard or contact limit/threshold can be defined using parameters such as but not limited to; 1) a specified percentage of surface area of the sensor 18 is in direct contact with the skin, 2) a specified force or pressure between the surface of the sensor 18 and the skin, 3) a specified level of moisture between the surface of the sensor 18 and the skin, and/or 4) a specified location of the sensor 18 with respect to an identified/desired location on the skin of the wearer. As such, it is recognised that the desired location and/or direct contact parameters of the sensors 18 can change over time (e.g. in real time) and thus the controller 14 can sense these changes in direct contact of the sensors 18 in view of the determined signal 6b quality. It is recognised that the degree of direct contact of the sensor 18 with the skin can be proportional with the conductivity between the sensor 18 and the skin and thus can be representative of the degree of quality (e.g. amplitude, presence of key signal features/characteristics, etc.) present in the collected signal(s) 6b. For example, in the extreme case of where the generator sensor 18a and/or the receiver sensor 18f are/is not in contact with the skin, the controller 14 would recognize the absence of any collected signal 6b in response to the generated signal 6a and thus would choose to deselect the currently utilized generator sensor 18a and/or the receiver sensor 18f and try again with a different sensor 18 pairing (e.g. retry with sensor 18b and 18f, retry with senor 18a and 18e, retry with and/or sensor 18b and 18g, etc.). Alternatively, for example, in the other extreme case of where the generator sensor 18a and/or the receiver sensor 18f are/is in acceptable contact with the skin, the controller 14 would recognize the collected signal 6b in response to the generated signal 6a as of acceptable quality and thus would choose to continue using the currently utilized generator sensor 18a and/or the receiver sensor 18f rather than try again with a different sensor 18 pairing (e.g. retry with sensor 18b and 18f, retry with senor 18a and 18e, retry with and/or sensor 18b and 18g, etc.). Alternatively, for example, in the intermediate case of where the generator sensor 18a and/or the receiver sensor 18f are/is in intermittent or otherwise borderline acceptable contact with the skin, the controller 14 would recognize the collected signal 6b in response to the generated signal 6a as of a borderline/acceptable/or unacceptable quality and thus would act accordingly (e.g. choose to continue using the currently utilized generator sensor 18a and/or the receiver sensor 18f or try again with a different sensor 18 pairing (e.g. retry with sensor 18b and 18f, retry with senor 18a and 18e, retry with and/or sensor 18b and 18g, etc.).

It is also recognised that the controller 14 could try different sensor 18 pairings in order to select the best received signal 6b for use as the reported signal 6b for that time period. In other words, the controller 14 could alternate the selected sensor 18 pairings using a selection frequency greater than the signal reporting frequency (i.e. the controller 14 tries 10 pairings in sequence and the picks the best signal 6b to report as representative for the 10 pairings). Accordingly, it is recognized that the controller 14 is continually monitoring the collected signal 6b quality and selecting/deselecting the sensor 18 pairings. Further, it is recognised that the sensor 18 parings can be a one to one (18a to 18e), a many to one (18a,b to 18e), or a one to many (18a to 18e,f) relationship as desired as applicable to the way in which the controller 14 is utilizing the system 19 to generate and collect the signals 6a,b deemed pertinent to the task at hand, e.g. collection of quality ECG signals.

In terms of the sensors 18 themselves, the materials of the fibres 24a can be conductive yarns that are knitted into the sensor 18. The shapes of the sensor can be circular or rectangular, for example having a contact conductive surface 40 and a backside insulated surface 42 (see FIGS. 3a,b) but the shapes don't matter as much since specific shapes can be selected/used for each application. This arrangement of the sensors 18 with the groupings 24,26 can covers the whole area around the heart horizontally (due to the sensor 18 size, number of sensors 18, distribution of the sensors 18 on the base fabric layer 13 and associated individual leads (e.g. conductive signal pathways/circuits 17 connecting the sensors 18 to the controller 14). It is recognised that the spacing 20 can be selected as a matter of density and resolution of the signals 6b that one wishes to capture via the controller 14. As further discussed below, the mechanism used by the controller 14 underlying all ECG signals 6a,b is based on calculating the potential between a pair of electrodes 18 as conducted via the body conductive pathway 7. Grouping electrodes in the two different groups 24,26 (e.g. two sides) can also help recording ECG signals 6b from different respective relative distances.

Figure 2:
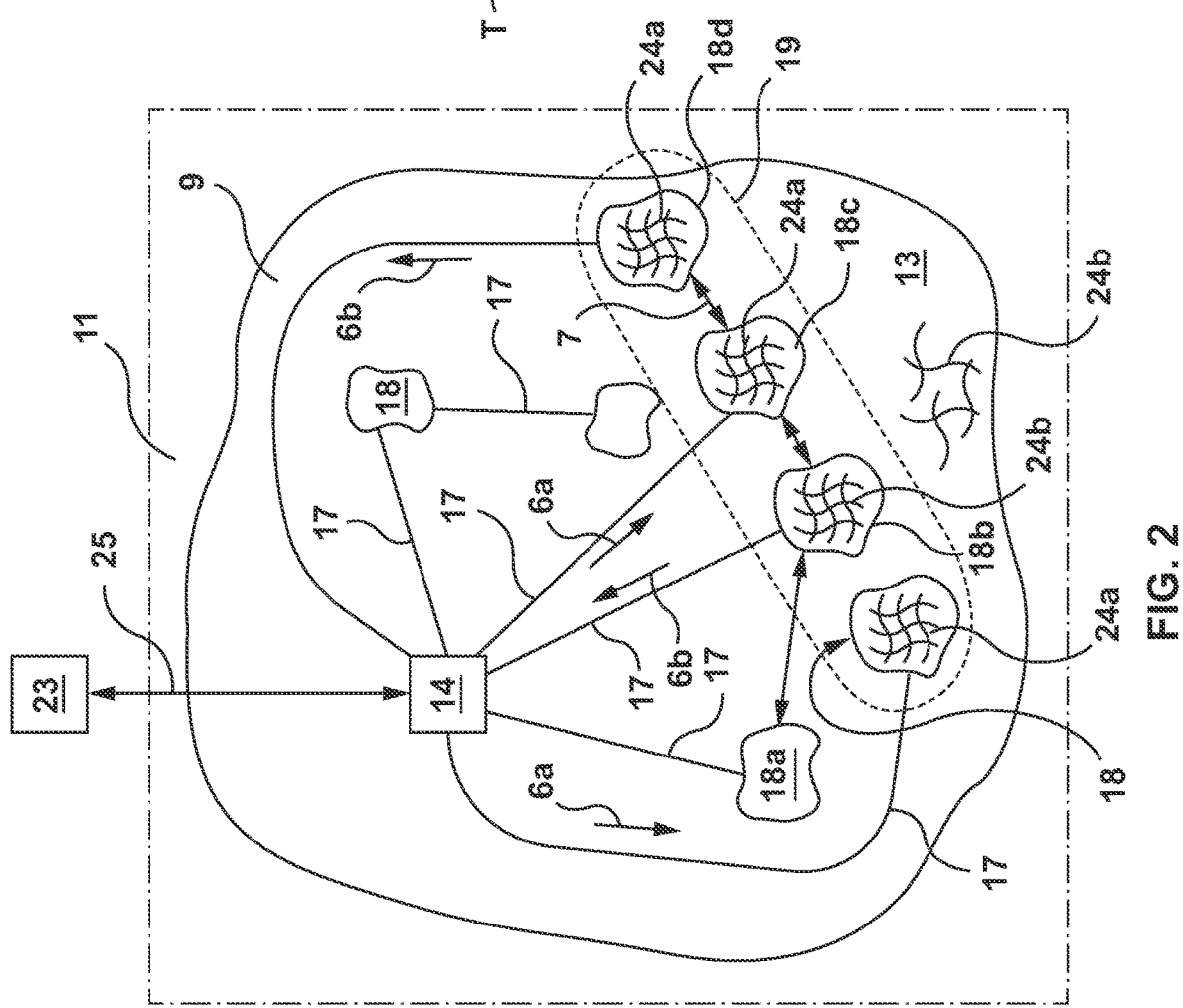

Referring again to FIGS. 2a,3a,b, preferably the side 10 and the side 12 of the fabric layer of the body 13 are situated in the same plane (e.g. a flat or curved fabric surface of thickness T—uniform or varied) in a composition of the textile computing platform 9 of the garment 11 (see FIG. 2). It is recognised that the sensors/actuators 18 of the textile based computing platform 9 can be formed as integral components of the interlacing of the fibres making up the body 13—see FIGS. 4a, 6, 7. The fabric of the body 13 can be comprised of interlaced resilient fibres 24b (e.g. stretchable natural and/or synthetic material and/or a combination of stretchable and non-stretchable materials, recognizing that at least some of the fibres comprising the sensors/actuators 18 are electrically conductive, i.e. metallic). It is also recognised that the fibres 24a making up the sensors 18 can be separate from the interlacing of the fibres 24b making up of the fabric body layer 13—see FIG. 4b, such that the fibres 24a of the sensor 18 are independently woven/knit from the fibres 24b and thus the already formed sensor 18 is applied to the already formed base fabric layer 13 as an applique or individual patch. In this example, the fibres 24a of the sensor 18 are non-integral with respect to the fibres 24b of the base fabric layer 13.

In view of the above, the multi sensor 18 textile-based ECG system 19 (e.g. in the form of a band) can be used to measure ECG signals 6b with appropriate resolution from different locations of the body 8 (based on the positioning of the sensors 18 within the garment/textile 11 as well as the positioning of the garment/textile 11 itself with respect to the body 8) to facilitate correct measurement when firm (i.e. deemed appropriate by the controller 14 via analysis of signal 6b quality) skin contact is not possible for all the electrodes 18 simultaneously. Furthermore, this system 19 can provide additional chances to collect desired ECG features for heart-related diagnosis which are not achievable by a single electrode. Accordingly, as shown, one embodiment of the textile computing platform 9 is as an ECG belt comprising multiple textile electrodes 18 with embedded electronics (e.g. controller 14) that provides continuous recording of ECG signals 6b from different locations on the body 8. The ECG belt 9 can not only provide a wearable that can be comfortably used on the daily basis by the wearer but can also record desired quality ECG signals 6b as deemed by the controller 14. The recorded signal 6b can be either saved on the SD card (electronics—e.g. memory 211—see FIG. 8) or shared through cloud web-service via communication between the controller 14 and a networked computer device 23 via the network 25—see FIG. 2. The textile computing platform 9 design, for example, can comprises 11 textile electrodes 18, (e.g. evenly) distributed via spacings 20, to provide a full spectrum ECG recording (see FIG. 8).

Further, it is advantageous as the textile computing platform 9 (e.g. belt) can be utilized for continuous recording of quality ECG signals 6b from multiple locations on the body 8, with being repositionable and/or reuseable. Therefore, this textile computing platform 9 can have huge implications for detection and diagnosis of heart-related disorders, e.g., cardiovascular disease, heart failure, postpericardiotomy syndrome, etc.

Figure 8:
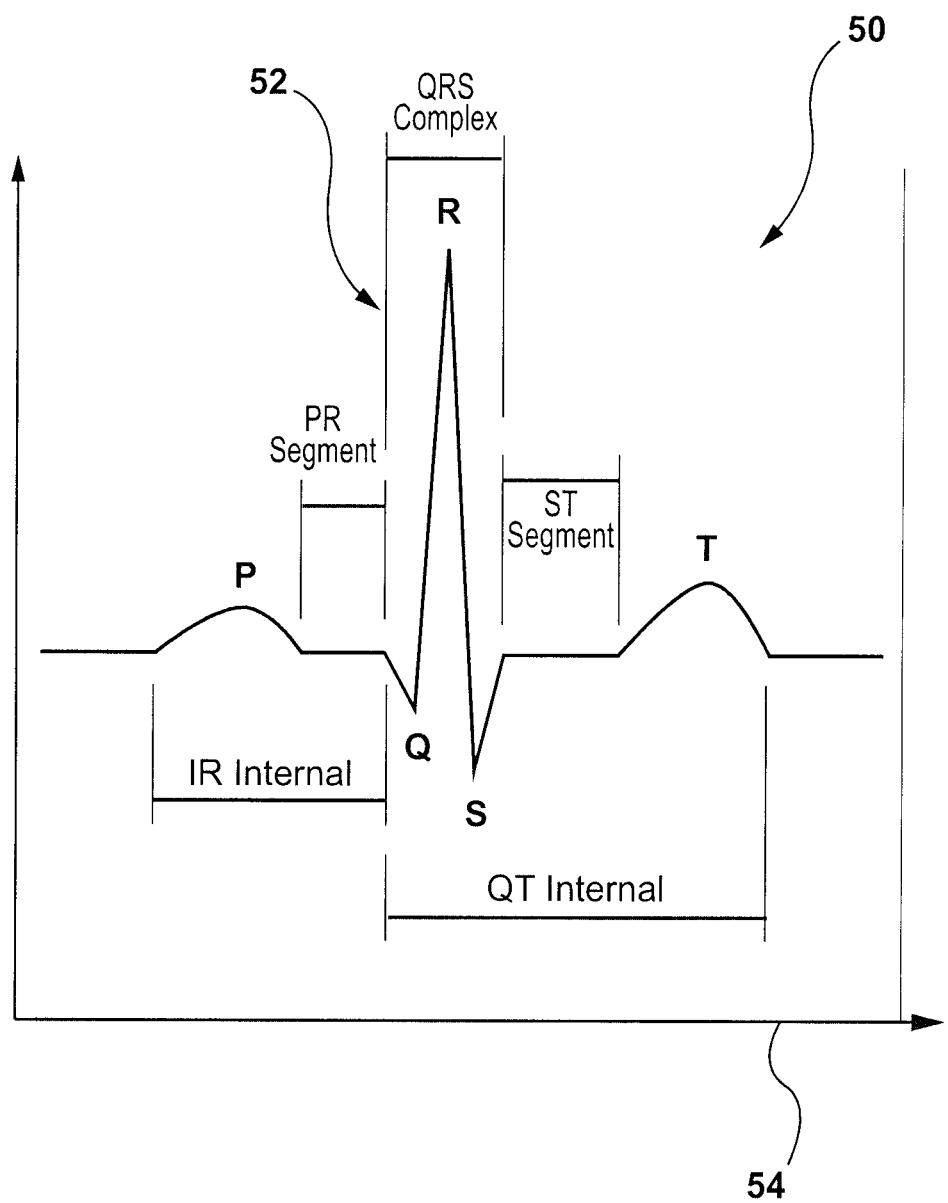
FIG. 8 is an example ECG trace representing the signals of the system of FIG. 1.

Features of the textile computing platform 9 can be features such as but not limited to: 1) the multi-sensor ECG band 9 provides capturing notable signal features of the heart signal 6b—see FIG. 8' 2) main advantages of our multi-sensor 18 strategy of the system 19 can be to increase the reliability of measuring system, by replacing/deselecting the lost/low quality signal/sensor 18 (weakness) with the another available/redundant sensor 18 and/or to increase the likelihood of extracting the main features of the heart signal 6b, ECG band 9 comprises for example 11 electrodes 18, distributed evenly (distance: 0.5 cm), connected to the corresponding electronics module 207 of the controller 14, textile electrodes 18 can be made of highly conductive silver yarns, surface resistivity is 30±15 Ohm (shape: e.g. circle with radius of 1.9 cm), and/or the textile electrodes 18 can be knitted/woven with different interlacing structures.

In view of the above, the system 19 disclosed herein can be implemented by a person and can include the garment 11 (e.g. suit or a belt/band) comprising a plurality of sensors 18 (e.g. textile-based ECG sensors) attached or otherwise embedded to/into fabric layer 13 of the garment 11 for measuring ECG activity (e.g. signals 6b) of the wearer. Generated/collected signals 6a,b of the sensors 18 can be sent/received via wires or cords (e.g. conductive pathway 17) to an electronic device (e.g. PCB) 14 attached via the electrical connectors 6 such as but not limited to snap type connectors (to fabric of the garment body layer 13 for transmitting (e.g. via a wireless network module 202—see FIG. 5) the information as sensor data to a computing device 200—see FIG. 9 (e.g. mobile device). The computing device 200 and/or the controller 14 can include a processor 208 for running an application 201 (e.g. ECG application) capable of interpreting the sensor 18 data.

For example, the application 201 can process the sensor 18 data to derive ECG recordings 50 (see FIG. 8) having various ECG features 52 collected over time 54. Capacitance and/or resistance (e.g. potential) can be measured across the body conductive pathway 7 between sensors 18 by the controller 14. For example, changes/absolute measurement (s) in resistance and/or capacitance (i.e. potential) can be measured using a bridge circuit (e.g. a Wheatstone bridge or Wien bridge) contained or otherwise sensed by the controller device 14, a type of electrical circuit in which two circuit branches are "bridged" by a third branch connected between the first two branches at some intermediate point along them. A source of power (e.g. a battery) of the controller device 14 can be connected to the bridge circuit along with a measuring device (e.g. a voltmeter, ammeter, or galvanometer) of the controller device 14 to detect the potential signals 6b in the conductive pathway 7 between selected sensors 18.

The electronic device 14 (e.g. controller 14) can be any device capable of being incorporated into a garment/textile 11 for receiving signals from one or more sensors 18 and transmitting the received signals (e.g. via a wireless transmitter) to the computing device 200. Non-limiting examples of an electronic device 14 according to the embodiments are a printed circuit board, RF module, transceiver module, and system-on-a-chip module. In one embodiment, the electronic device 14 can be an eight-channel printed circuit board having a Bluetooth low-energy wireless transmitter for transmitting the information received from a sensor 18 to the computing device 200. A power source of the controller 14, for example, can be attached via the connector(s) 6 to the garment body layer 13 for providing power to one or more sensors 18 and an electronic device 14 attached to the garment 11. In one embodiment, the power source can be a battery included within the electronic device 14. The power source can be actuated for example by an on-off switch connected to the power source and accessible to the wearer of the garment 11.

Application 201

The system can include an application 201 running on a computing device 200 and/or the controller 14 (e.g. smartphone or tablet) that can receive a transmission from the electronic device 14 of the garment 11 including sensor data 6b representative of information received by the electronic device 14 from one or more sensors 18 (e.g. ECG sensors) of the garment 11 and optionally orientation data generated by the electronic device 14. The data 6b (e.g. sensor data and/or orientation data in digital format) received by the computing device 200 from the electronic device 14 can be stored by the computing device 200 in memory 211 accessible by a processor 208 of the computing device 200 capable of running the application 201. Similarly, the controller 14 can have memory 211 accessible by a processor 208 of the computing device 200 capable of running the application 201.

The application 201 can be programmed to instruct the processor 208 to parse and/or interpret the sensor data 6b received from the sensors 18 of the garment 11, as well as to actuate various sensors 18 to generate signals 6a. For example, where a garment includes a plurality of sensors 18, the application 201 can parse the sensor data 6b into separate pools of data where each pool contains data collected by a different sensor 18 involving of one or more body 8 locations underlying the sensor(s) 18 on/in the layer 13 adjacent to the one or more body portions. The processor 208 can interpret the data from each pool to determine the pattern of activity collected by a single sensor 18 throughout the duration. For example, the application 201 can determine whether or not a particular sensor 18 was active (i.e. transmitted a signal 6b) during the ECG recording period and when during the recording the sensor 16 was active (e.g. in firm contact with the skin). If the processor 208 determines that a particular sensor 18 was active (i.e. transmitted a signal 6b to the electronic device 14) at a particular time during the recording period, then the processor 208 can further determine the magnitude of the signal 6b generated by the sensor 18 at that time as well as whether it contains the necessary ECG features 52 (e.g. peaks, intervals, etc.) within that recording period 54.

The application 201 can be executed as a set of instructions by a processor 208 of the computing device 200 and/or controller 14. Each of the modes (e.g. interaction mode; calibration mode) of the application 201 can also include a set of instructions for execution by the processor 208, and the processor 208 can communicate with each of the modes and/or components (e.g. 207) of the modes to execute the instructions. For example, in the "real-time" interaction mode the processor 208 can communicate with the electronics 207 of the to emit/receive signals 6a,b. Therefore, it will be understood that the application 201 includes executable instructions capable of generating/receiving sensor data 6a,b (and optionally orientation data) from selected sensors 18, to deselect or otherwise select alternative sensors 18 of the system 19 in the event certain sensor pairings are deemed of questionable or unacceptable quality, select multiple pairings of sensors 18 and decide what pairing provided the best/most desired signal 6b based on processing the received data to identify features 52 of the ECG recording 50 that are acceptable as compared to ECG feature models 56 stored in memory 211, and displaying the results of the processing to a user interface 204 of the computing device 14,200 for display to a user of the computing device 14,200.

In view of the above, it is recognised that the application 201 can be configured as a general activity (e.g. ECG) based application 201 that is for monitoring the ECG signals 6b of the specified body portions associated with the sensor(s) 18 in/on the garment fabric layer 13 adjacent to the body portion(s).

Figure 9:
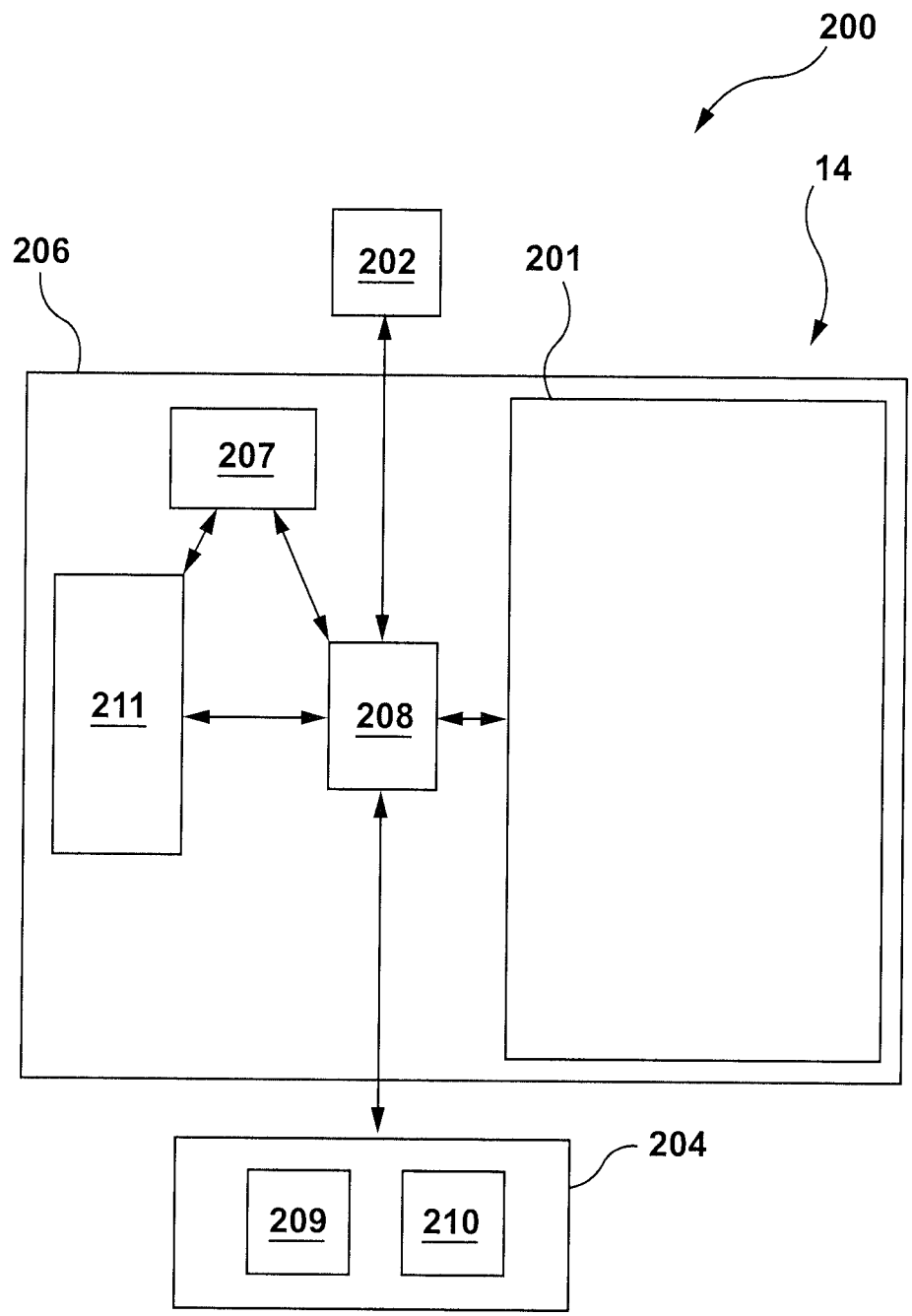
FIG. 9 is an example component view of a computer device of the system of FIG. 1.

Referring to FIG. 9, the computing device can be device 200. In some embodiments, the electronic device can be device 200. When electronic device is device 200, at least some of the sensor signal processing (and optionally the orientation data processing) can be done using the electronic device of the garment 11 before sending the processed information (e.g. as sensor data). The device 200 can configured to communicate over a communications network (e.g. Bluetooth, wireless network, etc.) with the connection interface 202 and thus via the controller 14. The application 201 can receive data entry by the user (e.g. via the user interface 204) and/or by another application running on the data processing system 206 for accessing the sensor data (e.g. processed or otherwise). The device 200 can be a land-based network-enabled personal computer. However, the invention is not limited for use with personal computers. For instance, the device 200 can comprise a wireless communications device, such as a wireless-enabled personal data assistant, a tablet, or mobile telephone if the communications network is configured to facilitate wireless data communication. In addition, the invention is not limited to only facilitating transmission of sensor data (and optionally orientation data) between the electronic device and computing device (e.g. device 200), and can be used to transmit raw data, processed sensor data, and/or any other multimedia data in addition or substitution of the sensor data, as desired. The device 200 can comprise a network interface 202, a user interface 204, and a data processing system 206 in communication with the network interface 202 and the user interface 204. Typically, the network interface 202 comprises an Ethernet network circuit card, however the network interface 202 may also comprise an RF antenna for wireless communication over the communications network. Preferably, the user interface 204 comprises a data entry device (such as keyboard 209, microphone or writing tablet), and a display device 210 (such as a CRT or LCD display). The user interface 204 can include one or more user input devices such as but not limited to a QWERTY keyboard (e.g. keyboard 209, a keypad, a stylus, a mouse, a microphone and the user output device such as an LCD screen display and/or a speaker. If the screen is touch sensitive, then the display can also be used as the user input device as controlled by the data processing system 206. The device 200 can include a network interface 202, such as a network interface card or a modem, coupled via connection to a data processing system 206. The network interface 202 is connectable during operation of the device 200 to the network (e.g. an Intranet and/or an extranet such as the Internet), which enables the device 200 to communicate with each other as appropriate. The network can support the communication of the network messages for the various transmitted data (e.g. sensor data) there between. The data processing system 206 can include a processor 208, and a non-volatile memory storage device (DISC) 211 (such as a magnetic disc memory or electronic memory) and a read/write memory (RAM) 211 both in communication with the processor 208. The DISC includes data which, when loaded into the memory 211, comprise processor instructions for the processor 208 which define memory objects for allowing the device 200 to communicate over the communications network. Operation of the device 200 is facilitated by the data processing system 206. The memory 212 is used to store data for access by the respective user and/or operating system/executable instructions of the device 2002. The processor 208 facilitates performance of the device 200 configured for the intended task through operation of the network interface 202, the user interface 204 and other application programs/hardware of the device 200 by executing task related instructions. These task related instructions can be provided by an operating system, and/or software applications located in the memory 212, and/or by operability that is configured into the electronic/digital circuitry of the processor(s) 208 designed to perform the specific task(s). Further, it is recognized that the data processing system 206 can include the computer readable storage medium 211 coupled to the processor 208 for providing instructions to the processor 208 and/or to load/update the instructions. The computer readable medium 211 can include hardware and/or software such as, by way of example only, magnetic disks, magnetic tape, optically readable medium such as CD/DVD ROMS, and memory cards. In each case, the computer readable medium 211 may take the form of a small disk, floppy diskette, cassette, hard disk drive, solid-state memory card, or RAM provided in the memory 211. It should be noted that the above listed example computer readable mediums 211 can be used either alone or in combination. Further, it is recognized that the device 200 can include the executable applications comprising code or machine readable instructions for implementing predetermined functions/operations including those of an operating system. The processor 208 as used herein is a configured device and/or set of machine-readable instructions for performing operations as described by example above. As used herein, the processor 208 may comprise any one or combination of, hardware, firmware, and/or software. The processor 208 acts upon information by manipulating, analyzing, modifying, converting or transmitting information for use by an executable procedure or an information device, and/or by routing the information with respect to an output device. The processor 208 may use or comprise the capabilities of a controller or microprocessor, for example.

Accordingly, any of the functionality of the executable instructions (e.g. through modules associated with selected tasks) may be implemented in hardware, software or a combination of both. Accordingly, the use of a processor 208 as a device and/or as a set of machine-readable instructions is hereafter referred to generically as a processor/module for sake of simplicity. The memory 211 is used to store data locally as well as to facilitate access to remote data stored on other devices connected to the network. The data can be stored in a table, which can be generically referred to as a physical/logical representation of a data structure for providing a specialized format for organizing and storing the data. General data structure types can include types such as but not limited to an array, a file, a record, a table, a tree, and so on. In general, any data structure is designed to organize data to suit a specific purpose so that the data can be accessed and worked with in appropriate ways. In the context of the present environment, the data structure may be selected or otherwise designed to store data for the purpose of working on the data with various algorithms executed by components of the executable instructions, depending upon the application thereof for the respective device 200. It is recognized that the terminology of a table/database is interchangeable with that of a data structure with reference to the components of the environment.

Figure 5:
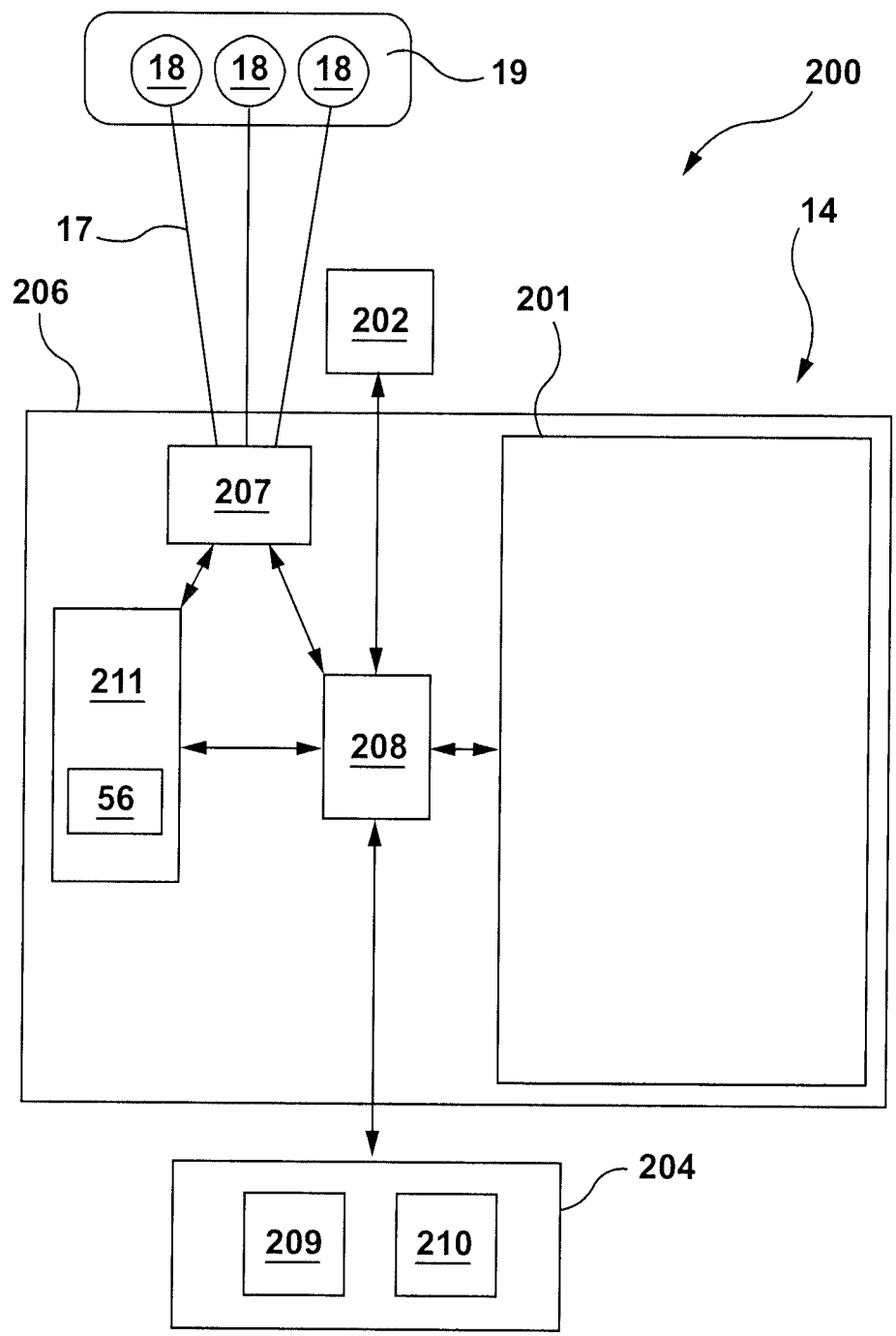
FIG. 5 is an example component view of a controller of the system of FIG. 1.

Referring to FIG. 5, the computing device can be the controller 14. When electronic device is controller 14, at least some of the sensor signal processing (and optionally the orientation data processing) can be done using the electronic device of the garment 11 before sending the processed information (e.g. as sensor data). The controller 14 can configured to communicate over a communications network (e.g. Bluetooth, wireless network, etc.) with the connection interface 202 and thus via the computing device 200. The application 201 can receive data entry by the user (e.g. via the user interface 204) and/or by another application running on the data processing system 206 for accessing the sensor data (e.g. processed or otherwise). The controller 14 can be a land-based network-enabled personal computer. However, the invention is not limited for use with personal computers. For instance, the controller 14 can comprise a wireless communications device, such as a wireless-enabled personal data assistant. In addition, the invention is not limited to only facilitating transmission of sensor data (and optionally orientation data) between the electronic device and computing device (e.g. device 200), and can be used to transmit raw data, processed sensor data, and/or any other multimedia data in addition or substitution of the sensor data, as desired. The controller 14 can comprise a network interface 202, a user interface 204, and a data processing system 206 in communication with the network interface 202 and the user interface 204. Typically, the network interface 202 comprises an Ethernet network circuit card, however the network interface 202 may also comprise an RF antenna for wireless communication over the communications network. Preferably, the user interface 204, optional for the controller 14, comprises a data entry device (such as keyboard 209, microphone or writing tablet), and a display device 210 (such as a CRT or LCD display). The user interface 204 can include one or more user input devices and the user output device such as an LCD screen display and/or a speaker. If the screen is touch sensitive, then the display can also be used as the user input device as controlled by the data processing system 206. The device 200 can include a network interface 202, such as a network interface card or a modem, coupled via connection to a data processing system 206. The network interface 202 is connectable during operation of the controller 14 to the network (e.g. an Intranet and/or an extranet such as the Internet), which enables the controller 14 to communicate with each other as appropriate. The network can support the communication of the network messages for the various transmitted data (e.g. sensor data) there between. The data processing system 206 can include a processor 208, and a non-volatile memory storage device (DISC) 211 (such as a magnetic disc memory or electronic memory) and a read/write memory (RAM) 211 both in communication with the processor 208. The DISC includes data which, when loaded into the memory 211, comprise processor instructions for the processor 208 which define memory objects for allowing the controller 14 to communicate over the communications network 25, as well as to interact with the sensors 18 of the textile computing platform 9. Operation of the controller 14 is facilitated by the data processing system 206. The memory 211 is used to store data for access by the respective user and/or operating system/executable instructions of the controller 14. The processor 208 facilitates performance of the controller 14 configured for the intended task through operation of the network interface 202, the user interface 204 and other application programs/hardware of the controller 14 by executing task related instructions. These task related instructions can be provided by an operating system, and/or software applications located in the memory 211, and/or by operability that is configured into the electronic/digital circuitry of the processor(s) 208 designed to perform the specific task(s). Further, it is recognized that the data processing system 206 can include the computer readable storage medium 211 coupled to the processor 208 for providing instructions to the processor 208 and/or to load/update the instructions. The computer readable medium 211 can include hardware and/or software such as, by way of example only, magnetic disks, magnetic tape, optically readable medium such as CD/DVD ROMS, and memory cards. In each case, the computer readable medium 211 may take the form of a small disk, floppy diskette, cassette, hard disk drive, solid-state memory card, or RAM provided in the memory 211. It should be noted that the above listed example computer readable mediums 211 can be used either alone or in combination. Further, it is recognized that the controller 14 can include the executable applications comprising code or machine readable instructions for implementing predetermined functions/operations including those of an operating system. The processor 208 as used herein is a configured device and/or set of machine-readable instructions for performing operations as described by example above. As used herein, the processor 208 may comprise any one or combination of, hardware, firmware, and/or software. The processor 208 acts upon information by manipulating, analyzing, modifying, converting or transmitting information for use by an executable procedure or an information device, and/or by routing the information with respect to an output device. The processor 208 may use or comprise the capabilities of a controller or microprocessor, for example. Accordingly, any of the functionality of the executable instructions (e.g. through modules associated with selected tasks) may be implemented in hardware, software or a combination of both. Accordingly, the use of a processor 208 as a device and/or as a set of machine-readable instructions is hereafter referred to generically as a processor/module for sake of simplicity. The memory 211 is used to store data locally as well as to facilitate access to remote data stored on other devices connected to the network. The data can be stored in a table, which can be generically referred to as a physical/logical representation of a data structure for providing a specialized format for organizing and storing the data. General data structure types can include types such as but not limited to an array, a file, a record, a table, a tree, and so on. In general, any data structure is designed to organize data to suit a specific purpose so that the data can be accessed and worked with in appropriate ways. In the context of the present environment, the data structure may be selected or otherwise designed to store data for the purpose of working on the data with various algorithms executed by components of the executable instructions, depending upon the application thereof for the respective controller 14. It is recognized that the terminology of a table/database is interchangeable with that of a data structure with reference to the components of the environment.

Electrocardiography (ECG or EKG) can be defined as the process of recording the electrical activity of the heart over a period of time using electrodes 18 placed over the skin of the body 8. These electrodes 18 can be used by the controller 14 detect the tiny electrical changes on the skin that arise from the heart muscle's electrophysiologic pattern of depolarizing and repolarizing during each heartbeat. It is very commonly performed to detect any cardiac problems. In a conventional 12-lead ECG, ten gel electrodes (i.e. non-textile based) are fixedly placed on the patient's limbs and on the surface of the chest. The overall magnitude of the heart's electrical potential is then measured from twelve different angles ("leads") and is recorded over a period of time (usually ten seconds). In this way, the overall magnitude and direction of the heart's electrical depolarization is captured at each moment throughout the cardiac cycle, in reliance on the fixed in contact and position of the gel electrodes, as facilitated by a clinician administering the ECG testing. The graph of voltage versus time produced by this noninvasive medical procedure is an electrocardiogram. In the conventional process, using gel electrodes, is such that the clinician can always rely upon each of the gel electrodes to respond (i.e. transmit when transmitting and receive when receiving) reliably. Therefore, in conventional gel based electrode procedures, deselection or otherwise selection of which sensors 18 to use as the best recorded signal 6a is not done, as it is unnecessary. Due to the guaranteed contact between the skin and the gel electrode. For instance, if the gel electrode stops working, the ECG test is stopped, the gel electrode reattached firmly, and the ECG testing continues. At no time during the traditional ECG test, using gel electrodes, does the clinician decide which of sensor pairings should be relied upon to provide the desired ECG signal. Therefore, the current system 19 can be different in that the degree skin contact of the textile-based sensors 18 can vary (e.g. from contact to no contact, from no contact to contact, and/or vary in contact quality) during the ECG testing period 54 (see FIG. 8).

Referring again to FIG. 8, in general there can be three main components 52 to an ECG signals 6b: the P wave, which represents the depolarization of the atria; the QRS complex, which represents the depolarization of the ventricles; and the T wave, which represents the repolarization of the ventricles. It can also be further broken down into the following components/features 52: O is the origin or datum point preceding the cycle, P is the atrial systole contraction pulse, Q is a downward deflection immediately preceding the ventricular contraction, R is the peak of the ventricular contraction, S is the downward deflection immediately after the ventricular contraction, T is the recovery of the ventricles, and U is the successor of the T wave but it is small and not always observed. Therefore, during each heartbeat, a healthy heart has an orderly progression of depolarization that starts with pacemaker cells in the sinoatrial node, spreads throughout the atrium, passes through the atrioventricular node down into the bundle of His and into the Purkinje fibers, spreading down and to the left throughout the ventricles. This orderly pattern of depolarization gives rise to the characteristic ECG tracing represented by the signals 6b. To the trained clinician, an ECG signal 6b conveys a large amount of information about the structure of the heart and the function of its electrical conduction system. Among other things, an ECG signal 6b can be used to measure the rate and rhythm of heartbeats, the size and position of the heart chambers, the presence of any damage to the heart's muscle cells or conduction system, the effects of heart drugs, and the function of implanted pacemakers. It is further recognised that the controller 14 via the electronics 207 provides for the fundamental component to an ECG as the instrumentation amplifier, which is responsible for taking the voltage difference between leads 17 of the sensors 18 and amplifying the signal 6b. ECG voltages as signals 6b measured across the body 8 can be on the order of hundreds of microvolts up to 1 millivolt (the small square on a standard ECG is 100 microvolts). This low voltage preferably relies upon a considered "low" noise circuit and instrumentation amplifiers of the electronics 207. The controller 14 can use analog-to-digital converters in the electronics 207 to convert the signal 6b to a digital signal that can then be manipulated with digital electronics. This can provide for digital recording of ECGs and use on computers.

The electronics 207 and/or the associated application 201 can include a rhythm analysis algorithm that produces a computerized interpretation of the ECG. The results from these algorithms can be considered "preliminary" until verified and/or modified by someone trained in interpreting ECGs. Included in this analysis can be the computation of common parameters 52 that include PR interval, QT interval, corrected QT (QTc) interval, PR axis, QRS axis, and more. Further, in ECG measurement, the electrodes/sensors 18 are the actual textile-based conductive pads attached to the body surface. Any pair of electrodes 18 can measure the electrical potential difference between the two corresponding locations of attachment via the body conductive pathway 7. Such a pair can be defined as forming a lead. However, "leads" can also be formed between a physical electrode and a virtual electrode, known as the Wilson's central terminal, whose potential is defined as the average potential measured by three limb electrodes that are attached to the right arm, the left arm, and the left foot, respectively.

Figure 6:
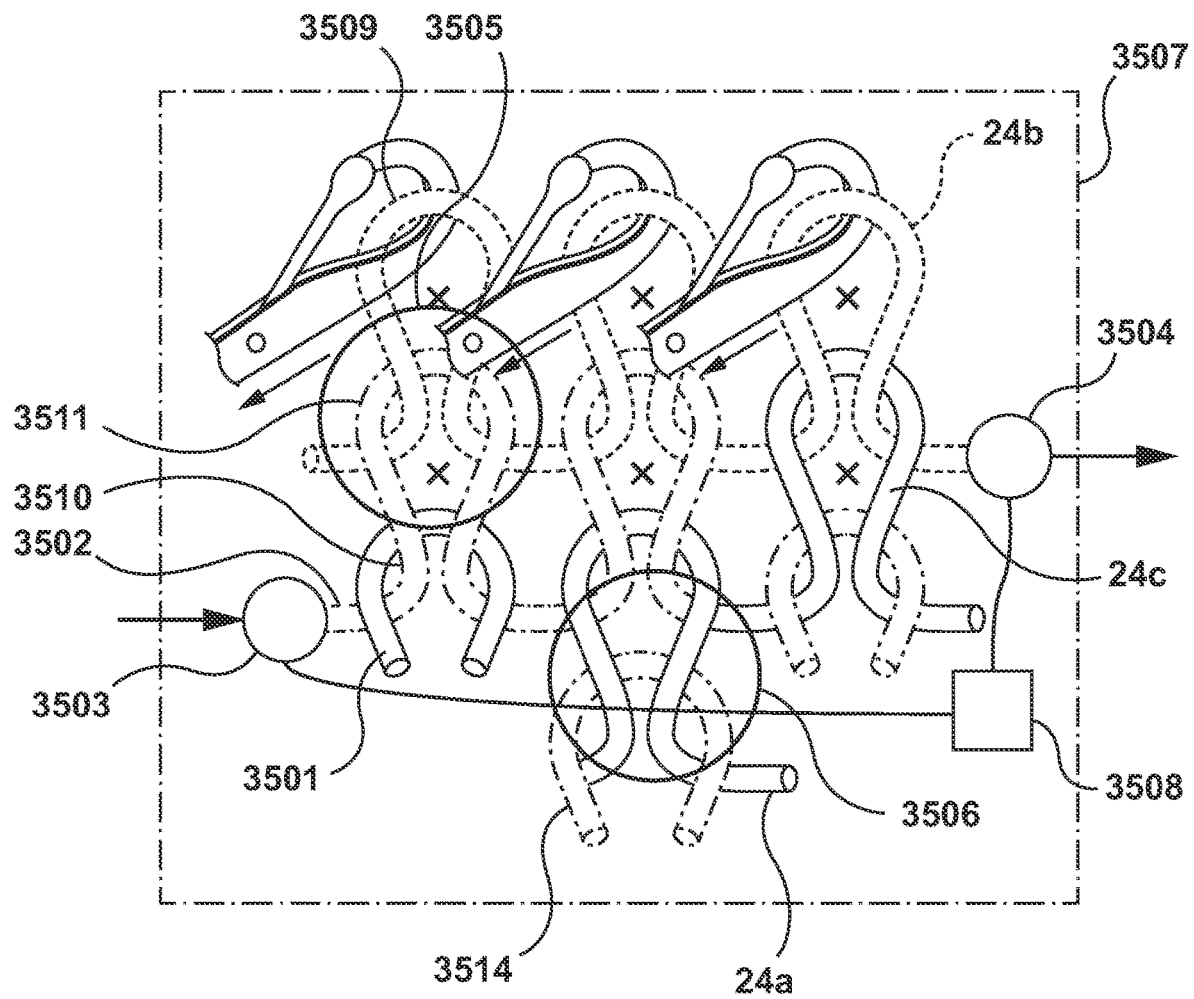
FIG. 6 is an embodiment of interlacing for the fibres of the textile of FIG. 1.

Referring to FIG. 6, shown is an exemplary knitted configuration for the sensors 18 of a network of electrically conductive fibres 3505 in, for example, a segment of an electrically conductive circuit 17 and/or sensor/actuator 18 (see FIG. 1). In this embodiment, an electric signal (e.g. current) is transmitted to conductive fibre 3502 from a power source (not shown) through a first connector 3505, as controlled by a controller 3508 (e.g. controller 14). The electric signal is transmitted along the electric pathway along conductive fibre 3502 past non-conductive fibre 3501 at junction point 3510. The electric signal is not propagated into non-conductive fibre 3501 at junction point 3510 because non-conductive fibre 3501 cannot conduct electricity. Junction point 3510 can refer to any point where adjacent conductive fibres and non-conductive fibres are contacting each other (e.g. touching). In the embodiment shown in FIG. 10, non-conductive fibre 3501 and conductive fibre 3502 are shown as being interlaced by being knitted together. Knitting is only one exemplary embodiment of interlacing adjacent conductive and non-conductive fibres. It should be noted that non-conductive fibres forming non-conductive network 3506 can be interlaced (e.g. by knitting, etc.). Non-conductive network 3506 can comprise non-conductive fibres (e.g. 3501) and conductive fibres (e.g. 3514) where the conductive fibre 3514 is electrically connected to conductive fibres transmitting the electric signal (e.g. 3502). For example, the interlacing method of the fibres in FIG. 6 can be referred to as weft knitting.

In the embodiment shown in FIG. 6, the electric signal continues to be transmitted from junction point 3510 along conductive fibre 3502 until it reaches connection point 3511. Here, the electric signal propagates laterally (e.g. transverse) from conductive fibre 3502 into conductive fibre 3509 because conductive fibre 3509 can conduct electricity. Connection point 3511 can refer to any point where adjacent conductive fibres (e.g. 3502 and 3509) are contacting each other (e.g. touching). In the embodiment shown in FIG. 6, conductive fibre 3502 and conductive fibre 3509 are shown as being interlaced by being knitted together. Again, knitting is only one exemplary embodiment of interlacing adjacent conductive fibres. The electric signal continues to be transmitted from connection point 3511 along the electric pathway to connector 3504. At least one fibre of network 3505 is attached to connector 3504 to transmit the electric signal from the electric pathway (e.g. network 3505) to connector 3504. Connector 3504 is connected to a power source (not shown) to complete the electric circuit.

Figure 7:
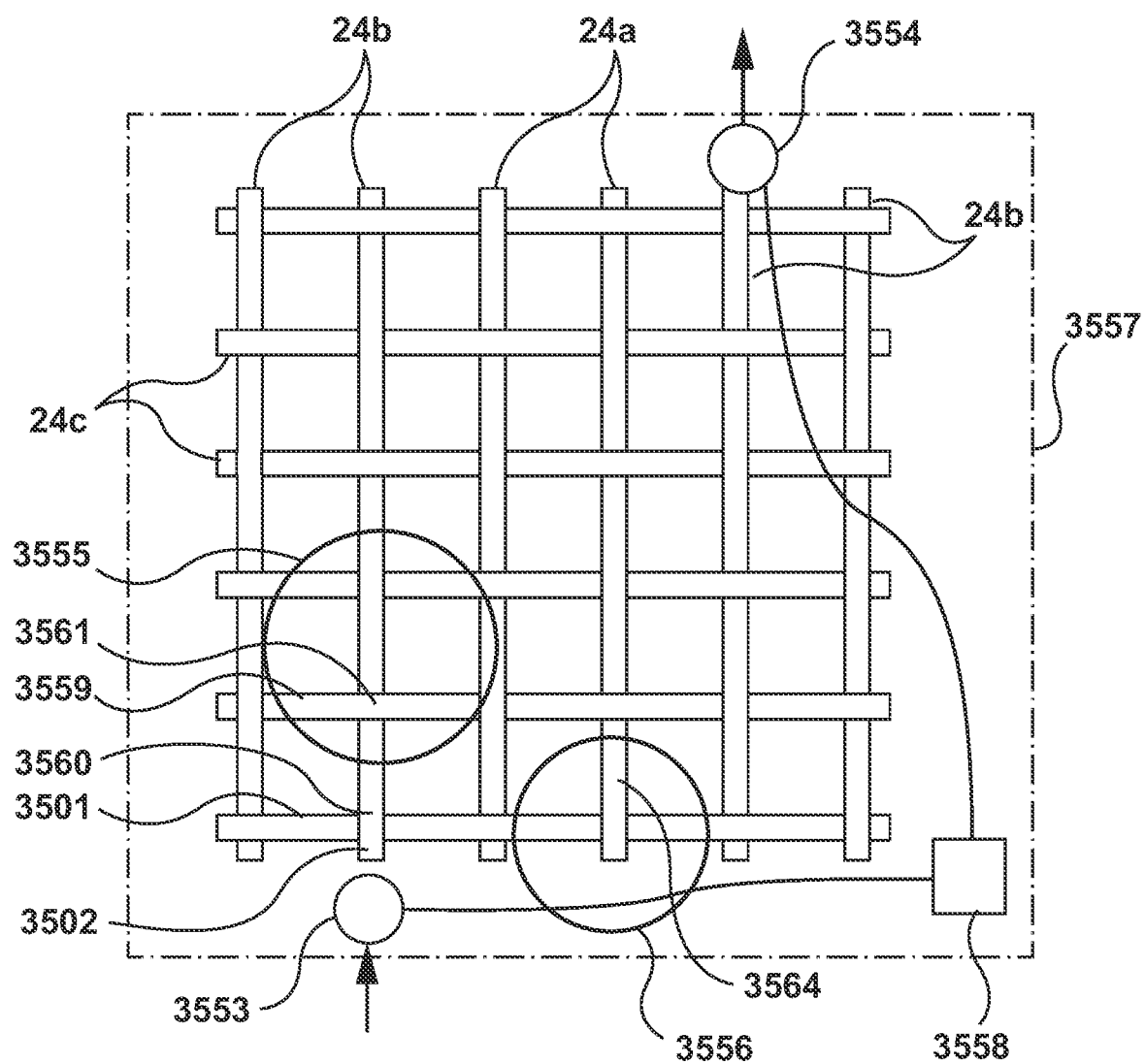
FIG. 7 is a further embodiment of interlacing for the fibres of the textile of FIG. 1.

FIG. 7 shows an exemplary woven configuration of a network of electrically conductive fibres 3555. In this embodiment, an electric signal (e.g. current) is transmitted to conductive fibre 3552 from a power source (not shown) through a first connector 3555, as controlled by a controller 3558 (e.g. controller 14). The electric signal is transmitted along the electric pathway along conductive fibre 3552 past non-conductive fibre 3551 at junction point 3560. The electric signal is not propagated into non-conductive fibre 3551 at junction point 3560 because non-conductive fibre 3551 cannot conduct electricity. Junction point 3560 can refer to any point where adjacent conductive fibres and non-conductive fibres are contacting each other (e.g. touching). In the embodiment shown in FIG. 20, non-conductive fibre 3551 and conductive fibre 3502 are shown as being interlaced by being woven together. Weaving is only one exemplary embodiment of interlacing adjacent conductive and non-conductive fibres. It should be noted that non-conductive fibres forming non-conductive network 3556 are also interlaced (e.g. by weaving, etc.). Non-conductive network 3556 can comprise non-conductive fibres (e.g. 3551 and 3564) and can also comprise conductive fibres that are not electrically connected to conductive fibres transmitting the electric signal. The electric signal continues to be transmitted from junction point 3560 along conductive fibre 3502 until it reaches connection point 3561. Here, the electric signal propagates laterally (e.g. transverse) from conductive fibre 3552 into conductive fibre 3559 because conductive fibre 3559 can conduct electricity. Connection point 3561 can refer to any point where adjacent conductive fibres (e.g. 3552 and 3559) are contacting each other (e.g. touching). In the embodiment shown in FIG. 7, conductive fibre 3552 and conductive fibre 3559 are shown as being interlaced by being woven together. The electric signal continues to be transmitted from connection point 3561 along the electric pathway through a plurality of connection points 3561 to connector 3554. At least one conductive fibre of network 3555 is attached to connector 3554 to transmit the electric signal from the electric pathway (e.g. network 3555) to connector 3554. Connector 3554 is connected to a power source (not shown) to complete the electric circuit. Again, weaving is only one exemplary embodiment of interlacing adjacent conductive fibres, such as fibres 24a,b as shown in demonstrating the interlacing technique of weaving the sensor 18 containing the fibres 24a as connected to the body 13 fibres 24b via connecting fibres 24c.

It is recognised that in general, a knit fabric is made up of one or more fibres formed into a series of loops that create rows and columns of vertically and horizontally interconnected stitches. A vertical column of stitches is called a wale, and a horizontal row of stitches is called a course.

In view of FIGS. 4a,4b and 6,7, the interlacing of the fibres 24a, 24b, 24c (optional) making the sensor 18 in combination with the fabric layer of the body 13 can be provided using knitting as the interlacing method via warp knitting (describing the direction in which the fabric is produced), also referred to as flat knitting, which is a family of knitting methods in which the fibres 24a, 24b, 24c zigzag along the length of the fabric (the combination of the wall structure 28 with the body 13), i.e. following adjacent columns, or wales, of knitting, rather than a single row (also referred to as weft knitting). A warp knit is made with multiple parallel fibres that are simultaneously looped vertically (at the same time) to form the fabric. A warp knit is typically produced on a flat-bed knitting machine, which delivers flat yardage. For example, a "Flat" or Vee Bed knitting machine can consists of 2 flat needle beds arranged in an upside-down "V" formation. These needle beds can be up to 2.5 metres wide. A carriage, also known as a Cambox or Head, moves backwards and forwards across these needle beds, working the needles to selectively, knit, tuck or transfer stitches. The flat knitting machine can provide for complex stitch designs, shaped knitting and precise width adjustment. Again as the name infers, flat bed are horizontal needle beds where the yarn is moved across the vee shaped needle bed within feeders.

For comparison, knitting across the width of the fabric is called weft knitting (also referred to as circular knitting), for example see FIG. 6. Contrary to warp knitting, weft knitting (describing the direction in which the fabric is produced) is such fabric made with a single yarn that's looped to create horizontal rows, or courses, with each row built on the previous row. A weft knits is typically performed on a circular knitting machine, which produces a tube of fabric. For example, circular, as the name infers, is knitting in the round. Here the yarn fed directly [up to 32 separate yarns] into the needle bed that spins around in one direction and creates a tube on fabric through the centre. Simultaneous construction of the desired sensor 18, in combination with the fabric layer of the body 13, cannot be performed as desired using circular knitting techniques. Accordingly, for interlacing done as knitting, warp knitting is needed to simultaneous construct the desired sensor 18 in combination with the fabric layer of the body 13

Further, interlacing of the fibres 24a, 24b, 24c (optional) making up the sensor 18 in combination with the fabric layer of the body 13 can be provided using weaving as the interlacing method, which is composed of a series of warp (lengthwise) fibres interlaced with a series of weft (crosswise) fibres. As such, in a woven fabric, the terms warp and weft refer to the direction of the two sets of fibres making up the fabric. As discussed, the sensors 18 can be integral with the interlacing of the fabric body layer 13. Alternatively, as discussed, the sensors 18 can be non-integral with the interlacing of the fabric body layer 13.

The invention claimed is:

1. An ECG sensor system comprising:
a substrate having a first side and a second side being opposed to the first side, the substrate of a non-conducting material;
a plurality of textile-based sensors positioned on the first side of the substrate, each of the plurality of textile-based sensors spaced apart from one another on the first side of the substrate, the second side of the substrate opposing the first side and covering one side of each of the plurality of textile-based sensors as an insulating covering, the insulating covering including non-conductive fibres, and wherein each of the plurality of textile-based sensors includes conductive fibres interlaced with one another; and
a conductive trace connected to the each of the plurality of textile-based sensors, each of the conductive traces for connecting the plurality of textile-based sensors to controller device for sending and receiving electronic signals from a selected pair of the plurality of textile-based sensors to measure an ECG of a wearer,
wherein said plurality of textile-based sensors includes at least one textile-based ECG generator electrode for transmitting a controller-generated signal generated by the controller device through skin of a user, and least one textile-based ECG receiver electrode spaced apart from the textile-based ECG generator electrode, said at least one ECG receiver electrode configured to sense the controller-generated signal through said skin of said user,
wherein said controller device is configured to:
generate said controller-generated signal;
transmit said controller-generated signal through said at least one textile-based ECG generator electrode;
sense said controller-generated signal from said at least one textile-based ECG generator electrode via said at least one textile-based ECG receiver electrode;
based on said sensing said controller-generated signal, generated by said controller device, and transmitted by said at least one textile-based ECG receiver electrode, determine that said at least one textile-based ECG generator electrode and/or said at least one textile-based ECG receiver electrode is causing said controller-generated signal that is transmitted through the at least one of the textile-based ECG generator electrode to be of unacceptable signal quality;
de-select said at least one textile-based ECG generator electrode and/or said at least one textile based ECG receiver electrode, and select another textile-based ECG generator electrode and/or ECG receiver electrode; and
repeat said generating of the controller-generated signal and said sensing of said controller-generated signal using the another textile-based ECG generator electrode and/or ECG receiver electrode.

2. The ECG sensor system of claim 1, wherein the non-conducting material is a non-interlaced material such as plastic.

3. The ECG sensor system of claim 1, wherein the non-conducting material includes non-conductive fibres as an interlaced material selected from the group consisting of: a woven material and a knit material.

4. The ECG sensor system of claim 1, wherein the substrate is in the form of a band and the plurality of textile-based sensors are distributed along the band.

5. The ECG sensor system of claim 1, wherein the plurality of textile-based sensors are divided into a generator group and a receiver group, such that a group spacing between a generator sensor of the generator group and a receiver sensor of the receiver group is larger than spacing between the sensors within the generator group and spacing between the sensors within the receiver group, the generator sensor being adjacent to the receiver sensor.

6. The ECG sensor system of claim 3, wherein the conductive fibres and the non-conductive fibres are interlaced with one another to form an integral interlaced structure.

7. The ECG sensor system of claim 3, wherein the conductive fibres and the non-conductive fibres are connected to one another forming a non-integral structure, such as an applique.

8. The ECG sensor system of claim 6, wherein respective conducting surfaces of the plurality of textile-based sensors is raised from a surrounding insulating surface of the first side.

9. The ECG sensor system of claim 1 further comprising the controller device configured via stored instructions for execution by a computer processor for deselecting at least one of the sensors from the selected pair and selecting a replacement sensor from the plurality of textile-based sensors, a basis for said deselecting based on analysis of a quality of the electronic signals.

10. The ECG sensor system of claim 1 further comprising the controller device configured via stored instructions for execution by a computer processor for alternating different pairings from the plurality of textile-based sensors as the select pair and choosing a determined optimum signal from the electronic signals received from the alternating different pairings.

11. The ECG sensor system of claim 7, wherein respective conducting surfaces of the plurality of textile-based sensors is raised from a surrounding insulating surface of the first side.

* * * * *